United States Patent
Benning et al.

(10) Patent No.: US 7,527,618 B2
(45) Date of Patent: May 5, 2009

(54) HYGIENIC ARTICLE FOR INCONTINENCE

(75) Inventors: Markus Benning, Gerstetten (DE); Rüdiger Kesselmeier, Nattheim (DE); Christian Koch, Bachhagel (DE); Wolfgang Röhrl, Herbrechtingen (DE)

(73) Assignee: Paul Hartmann AG, Heidenheim (DE)

( * ) Notice: Subject to any disclaimer, the term of this patent is extended or adjusted under 35 U.S.C. 154(b) by 569 days.

(21) Appl. No.: 11/111,312

(22) Filed: Apr. 21, 2005

(65) Prior Publication Data

US 2005/0256496 A1 Nov. 17, 2005

Related U.S. Application Data

(60) Provisional application No. 60/565,239, filed on Apr. 23, 2004.

(51) Int. Cl.
*A61F 13/15* (2006.01)
(52) U.S. Cl. .................. 604/392; 604/385.201
(58) Field of Classification Search .......... 604/385.201, 604/389–392
See application file for complete search history.

(56) References Cited

U.S. PATENT DOCUMENTS

| | | | | |
|---|---|---|---|---|
| 4,670,012 | A | * | 6/1987 | Johnson ................... 604/390 |
| 6,626,881 | B2 | * | 9/2003 | Shingu et al. ......... 604/385.201 |
| 2003/0199843 | A1 | | 10/2003 | Kato et al. |
| 2005/0143709 | A1 | * | 6/2005 | Lindstrom ................. 604/391 |

FOREIGN PATENT DOCUMENTS

| | | |
|---|---|---|
| DE | 19732499 C2 | 5/2001 |
| DE | 69625479 T2 | 5/2003 |
| DE | 10140621 A1 | 7/2003 |
| DE | 10196884 T5 | 4/2004 |
| EP | 1110529 A1 | 12/2000 |
| EP | 1269949 A2 | 6/2002 |
| EP | 1413277 A1 | 10/2003 |
| WO | WO02/069866 A1 | 9/2002 |

OTHER PUBLICATIONS

German Patent Office Search Report—Published Dec. 10, 2004.

* cited by examiner

*Primary Examiner*—T. Zalukaeva
*Assistant Examiner*—Lynne Anderson
(74) *Attorney, Agent, or Firm*—YoungBasile,

(57) ABSTRACT

An absorbent incontinence article has a main body portion consisting of a front region, a back region and an interposed crotch region lying therebetween in a longitudinal direction when finally positioned between the legs of a wearer. The main body portion includes an absorbent core and material sections attached to at least one of the back and front regions which extend in the transverse direction beyond lateral lengthwise edges of the main body portion and connect the front region and the back region. The sections of material are folded over themselves along at least one lengthwise direction extending fold line. Partial sections of the material sections adjoining one another over an area in the folded configuration are releasably attached to one another at affixation points.

24 Claims, 7 Drawing Sheets

HYGIENIC ARTICLE FOR INCONTINENCE

CROSS REFERENCE TO COPENDING APPLICATION

This application claims the benefit of the filing date of copending U.S. Provisional Patent Application Ser. No. 60/565,239, filed Apr. 23, 2004, the contents of which are incorporated herein in its entirety.

BACKGROUND

The present invention relates to an absorbent incontinence article, specifically for incontinent adults, with a main body portion consisting of a front region, a back region and a crotch region located between them in the longitudinal direction which is finally positioned between the legs of a wearer, wherein the main body portion comprises an absorbent core, and having material sections attached to the rear region and/or the front region which extend in the transverse or hip-encircling direction beyond lateral lengthwise edges of the main part and connect the front region and the rear region when the article is worn.

In the case of incontinence articles of this type, the material sections, particularly those attached only to the rear region, can be formed of another material than the main body portion or a component of the main body portion, for example a fluid-impermeable backsheet or a fluid-permeable topsheet. For example, the material section forming the side parts on the incontinence article, often described as "wings," can breathe, in particular, can be configured to be air- and vapor-permeable, whereas the main body portion, often described as the chassis, can be configured to be fluid-impermeable, in particular, impermeable to moisture. To close the incontinence article, the material sections forming the lateral parts, preferably non-releasably attached to the rear region, are wrapped across the torso of the wearer and releasably connected to the main body portion, preferably to the outside of the front region of the garment-facing main body portion. Mechanical or adhesive closures on the lateral parts of the incontinence article are frequently used, which act in concert with similarly configured landing zones in the front region of the main body portion.

EP 1 269 949 A2 does not show an incontinence article in which the side parts projecting from a back region are fastened to a front region; rather it shows a T-shaped diaper in which the side parts projecting from the back region are connected to each other to form an opening for the hips which is completely closed in the circumferential direction. The lateral parts projecting laterally from the back region to form the hip belt are folded over each other in a Z-shape and are only temporarily attached to each other in this configuration, only during manufacture of the article within the machine.

Taking an absorbent incontinence article of the type initially described as the starting point which has relatively wide material sections attached to the main body portion, it would be desirable to improve the handling of these material sections during production in a high-speed machine and to make handling the incontinence article as user-friendly as possible when it is employed by the wearer or by care-givers.

SUMMARY

An absorbent incontinence article of the type initially described, has the material sections which are folded over themselves at least along one fold line running in the longitudinal direction and partial sections of the material sections, folded over each other and contacting each other over large areas in this folded configuration, and are releasably attached at affixation point or areas.

While the hip belt on T-shaped diapers is relatively narrow, it is desirable for absorbent incontinence articles of the type initially described to have fairly wide lateral material sections. Under the present invention, an incontinence article has been created in which the material sections folded over each other are releasably attached to each other so that they are kept in their folded configuration in the high-speed manufacturing machine and do not flutter. Even when the hygiene article is removed from the packaging and is being prepared for application, the releasable attachment of the folded material sections proves advantageous. It makes the incontinence article user-friendly and it proves particularly advantageous when used on persons requiring a high degree of personal care. For example, the incontinence article is frequently applied to patients requiring care who are lying on their side. In this situation, one of the material sections projecting laterally beyond the main body portion must be fed under the patient. This process of feeding the section under the patient is considerably simplified with releasably attached material sections in accordance with the invention.

The aforementioned releasable attachment of the folded partial sections of the material sections attached to the main body portion can be achieved, for example, by cold stamping or by stamping using temperature (thermal welding), by needling, in particular hot needling, or by ultrasonic welding or laser welding or similarly effective joining methods.

BRIEF DESCRIPTION OF THE DRAWING

Additional features, details and advantages of the invention can be found in the attached claims, the drawing and following description of a preferred embodiment of the invention.

DETAILED DESCRIPTION

Figure 1A:
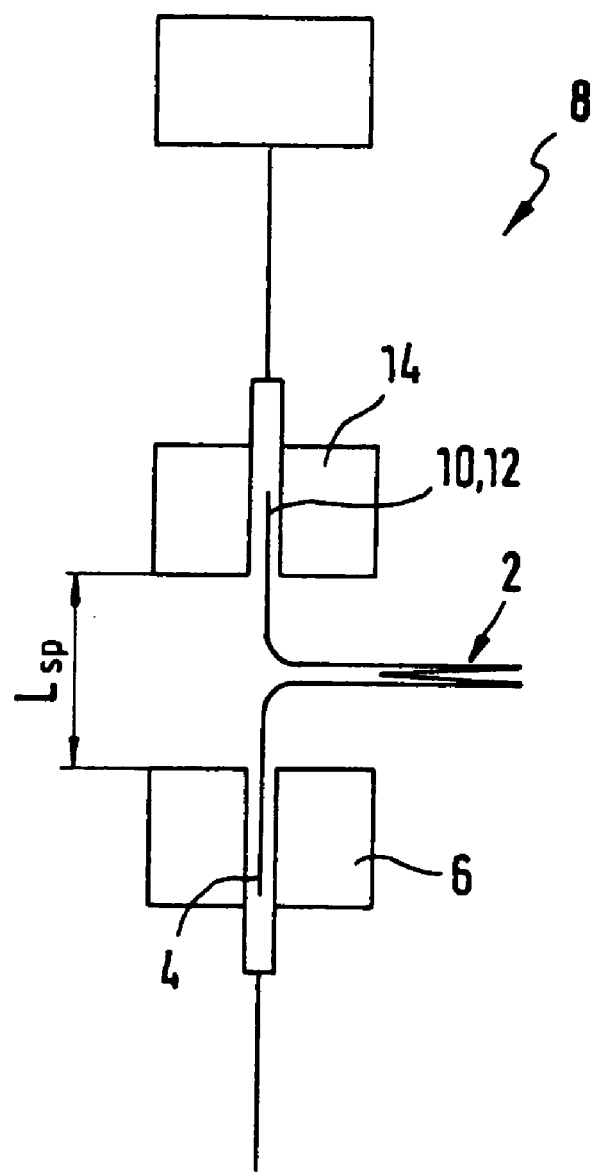
FIG. 1a shows a schematic representation of the section of material clamped in a tension testing device.

In one specific aspect of the invention it proves to be advantageous if a gripping area to unfold the material section is provided on one part of a thusly folded material section which forms the open end of the material section in the transverse direction. In its simplest form, this gripping area can be formed by a longitudinal edge section of the aforementioned part which a wearer can grasp with his fingers. It would also be conceivable to provide a separate element which could be grasped manually, a step which would, however, mean additional manufacturing complexity.

Furthermore it proves expedient for handling that the section in question has no affixation points in the gripping area, that it is not attached or joined there to other sections or to the main body portion in a manner which would prevent a wearer from grasping it or make it more difficult for a wearer to grasp. The invention also contemplates that the wearer inserts his fingers or uses his fingers to reach between individual affixation points to grasp the gripping area and then to unfold the material section by pulling to release the affixation points.

In this connection it is advantageous in accordance with a particularly advantageous and preferred further embodiment of the incontinence article under the invention that the releasable attachment at all the affixation points or areas is separable by a single pull on the gripping area of the material section in question. This makes handling even simpler, and the incontinence article proves even more user-friendly with respect to its use on persons who require intensive care.

The aforementioned single pull on a gripping area, a complete unfolding of the folded material sections achieved as the result of a single pulling motion, means that the wearer does not need to pull or tug violently several times on a particular material section until all the affixation points between the parts of the material section and possibly to the main body portion of the incontinence article are broken.

In the simplest instance, any material section is folded over itself along a fold line, so that two partial sections lie on top of each other, or abut each other. Preferably the material section is folded over itself along at least two fold lines so that a configuration with a Z-shaped cross section results. In accordance with a further preferred embodiment, the material sections are folded over themselves along three fold lines. In accordance with a still further preferred embodiment, the material sections are folded over themselves along four fold lines.

In accordance with a further aspect of the incontinence article under the invention, the gripping areas are turned outward before the material sections are unfolded, that is, turned away from each other and from a lengthwise center axis of the main part of the diaper when spread out on a flat surface so that the wearer can comfortably grasp them with the left hand from the left and the right hand from the right.

The releasable attachment to each other of the parts of the material sections folded over each other and possibly also to the main body portion is preferably formed by several essentially punctiform affixation points. A punctiform affixation point of the aforementioned type means that the affixation point has an area (projected on the x-y plane of the main body portion) of less than 5 mm$^2$, specifically of less than 2 mm$^2$ and even more specifically of less than 1 mm$^2$. The affixation points do not have to be strictly punctiform or circular. Shapes deviating from a dot or circle can also be contemplated and are advantageous, such as triangles, rectangles, polygons or ovals. Preferably the releasable attachment to each other of the parts of the material sections folded over each other is by punctiform affixation points created thermally or ultrasonically.

It was recognized as part of the invention that the number, the distribution or the relative surface area of the affixation points, or the adhesive strength of the releasably attached parts can be selected in such a way that the releasable attachment can be separated at all the affixation points or areas when unfolding the article by a single pull on the specific gripping area of the material sections. This can be aided in an advantageous way by the number or the relative surface area of the affixation points or the adhesive strength of the releasably attached parts as the distance from the gripping area of the material section decreases. It was recognized as part of the invention that the farther an area of the parts of the material sections folded over each other is removed from the gripping area, the lower the strength of the bond of the parts to each other should be in order to achieve a separation of all the affixation points or areas through a single pull on the particular gripping area of the material sections, i.e., through a single unfolding motion. It was consequently also recognized that it is not difficult to configure the releasable attachment of the folded parts to be sufficiently strong in the proximity of the gripping area. This ensures that flat material webs, which have preferably been folded before or in the high-speed production machinery, can be transported safely without material sections projecting laterally from the main body portion part of the incontinence article fluttering or parts folded over each other being displaced inside the fold. The result is a neat appearance, even when the entire product is later folded.

In a further aspect of the invention it proves advantageous if the parts abutting each other are not joined to each other over a compass of 1.5 cm from a point on the preferably most distant fold line; this point is farthest removed from the gripping area in the planar direction of the folded configuration. This most distant point will be a point of the fold line lying at the open edge of the material sections. But even over the entire extension of the fold line under consideration, specifically the one farthest removed from the gripping area, it proves advantageous if the adjoining partial sections are not attached to one another at a distance of 5 mm, specifically of 8 mm, and even more specifically of 10 mm from this fold line.

It proves furthermore advantageous if the surface extent of the parts folded over each other and adjoining each other can be divided (mentally) into two approximately equal halves by a straight line running in the lengthwise direction and if the number, or the relative surface area of the affixation points or areas, or the adhesive strength of the releasably attached parts is different in these two halves. It proves to be particularly advantageous if the number or the relative surface area of the affixation points or the adhesive strength of the releasably attached parts in the half facing the gripping area in the lateral direction, that is the adjacent half, is greater than in the half facing away from the gripping area in the lateral direction.

The material sections attached to the main body portion of the incontinence article are, as mentioned at the outset, wider (transverse to the direction around the hips) than is normally the case with typical T-shaped diapers. The width, or the extension of a material section in the lengthwise direction of the hygiene article, is preferably at least 10 cm in the area of the attachment to the main body portion, specifically at least 14 cm, specifically at least 18 cm and even more specifically at least 22 cm.

The extension of a material section attached to the main body portion in the unfolded state in the transverse direction beyond the lengthwise edge of the main body portion, which corresponds to the direction around the hips when the article is worn, measures at least 10 cm, specifically at least 15 cm and even more specifically at least 18 cm. It preferably measures 35 cm at the most, specifically 30 cm at the most and even more specifically 27 cm at the most. It can also be contemplated and is advantageous for individual incontinence articles if such material sections projecting laterally from the main body portion are attached both in the front region and in the back region. In this instance it proves advantageous if all such material sections of the incontinence article are folded in the sense of the invention and removably attached.

To close the incontinence article when it is worn by a user, the material sections have closures which can be designed to grip mechanically or adhesively and which for their part are advantageously arranged in a folded configuration on the material sections and can be unfolded for use. It proves expedient if the material sections in the back region have closures of a type which can act in concert in a releasably gripping or adhering fashion with a landing zone on the main part of the diaper.

It also proves advantageous if the material sections provided on both sides in the front region and/or in the back region of an incontinence article which is folded before it is used are folded in on the body-facing side of the main body portion. The folded-in material sections can partially overlap one another, but their gripping areas can be grasped at the same time, that is, they can be perceived visually and can be grasped by hand.

The material sections attached to the main body portion are preferably of a non-woven material, specifically and preferably spunbond materials (S), or spunbond-meltblown materials (SM), or meltblown layers (SMS) coated on both sides with spunbond material layers, or carded non-woven materials can be used. Non-woven laminates, in particular, double-layer, triple-layer or multi-layer combinations of the aforementioned non-woven materials can be used. The individual layers can be joined by using normal and known methods, for example, thermal bonding (welding, in particular, laser welding, hot-melt, air-through) or ultrasonic welding procedures; cold compression, needling, sewing or bonding of non-woven materials can also be contemplated. Joining to textile woven fabrics, non-crimp fabrics or knitted fabrics, that is with materials exhibiting a textile bond in the broadest sense, can also be contemplated. Preferably the material sections attached laterally to the main body portion are configured to breathe at least in sections, with microporosity, which allows an exchange of air as well permeability for moisture in the form of vapor, being regarded as advantageous. The material sections advantageously have a surface weight of 10 to 150 g/m$^2$, in particular 20-100 g/m$^2$, and specifically of 25-50 g/m$^2$.

The material sections attached to the main body portion can be configured in accordance with another aspect of the invention in such a way that the sections are less rigid than the main body portion or the chassis-forming materials of the main part, such as in particular the backsheet or a laminate of the main part consisting of the backsheet and topsheet. In this way a skin-friendly side section of the hygienic article can be achieved, which preferably suggests a woven or a non-woven material and is experienced as pleasant by the wearer.

In accordance with an autonomous inventive aspect, it proves particularly advantageous that, when the material sections are unfolded by pulling at the appropriate gripping area, the affixation points or areas offer a peak resistance of 2.5 N maximum, specifically of 2.4 N maximum, specifically of 2.3 N maximum, specifically of 2.2 N maximum, specifically of 2.1 N maximum, and further specifically of 2.4 N maximum, averaged over the unfolding process. If the tensile force when pulling on the appropriate gripping area is registered at each moment during an unfolding process, and if the peaks which differ by at least 0.5 N from immediately adjacent, neighboring areas are considered, all the peaks registered during an unfolding process can be averaged, that is a peak effort averaged over the number of these peaks can be calculated.

If not just one unfolding procedure is taken into consideration, but six unfolding procedures of six identically configured and folded material sections and the peak forces over the six unfolding procedures are averaged in the same way as the previously determined, averaged peak forces, they read 2.0 N maximum, specifically 1.8 N maximum, specifically 2.3 N maximum, specifically 1.7 N maximum, specifically 1.6 N maximum, and further specifically 1.5 N maximum, It furthermore proves particularly advantageous that in accordance with a further intrinsically independent inventive aspect, the material sections are folded and pre-adhered in such a way that the effort required when unfolding a material section in one pull averaged over six unfolding procedures reads 120 Nmm maximum, specifically 115 Nmm maximum, specifically 110 Nmm maximum, specifically 105 Nmm maximum, specifically 100 Nmm maximum, specifically 95 Nmm maximum.

In another aspect, incontinence articles formulated independently of one another, in which the releasable attachment is implemented in such a way that they satisfy the requirements in high-speed manufacturing machines on the one hand and permit easy handling by the wearer or health-care personnel on the other, the force required for the unfolding of the material sections and the resulting effort lying within the claimed ranges.

In what follows, a test is described for determining the forces to be overcome when unfolding the material sections folded over themselves and for testing the unfolding of the material sections in one pull. The force occurring at each moment over the opening distance is determined and recorded using a tension testing apparatus in accordance with EN ISO 527-1 (April 1996).

Figure 1B:
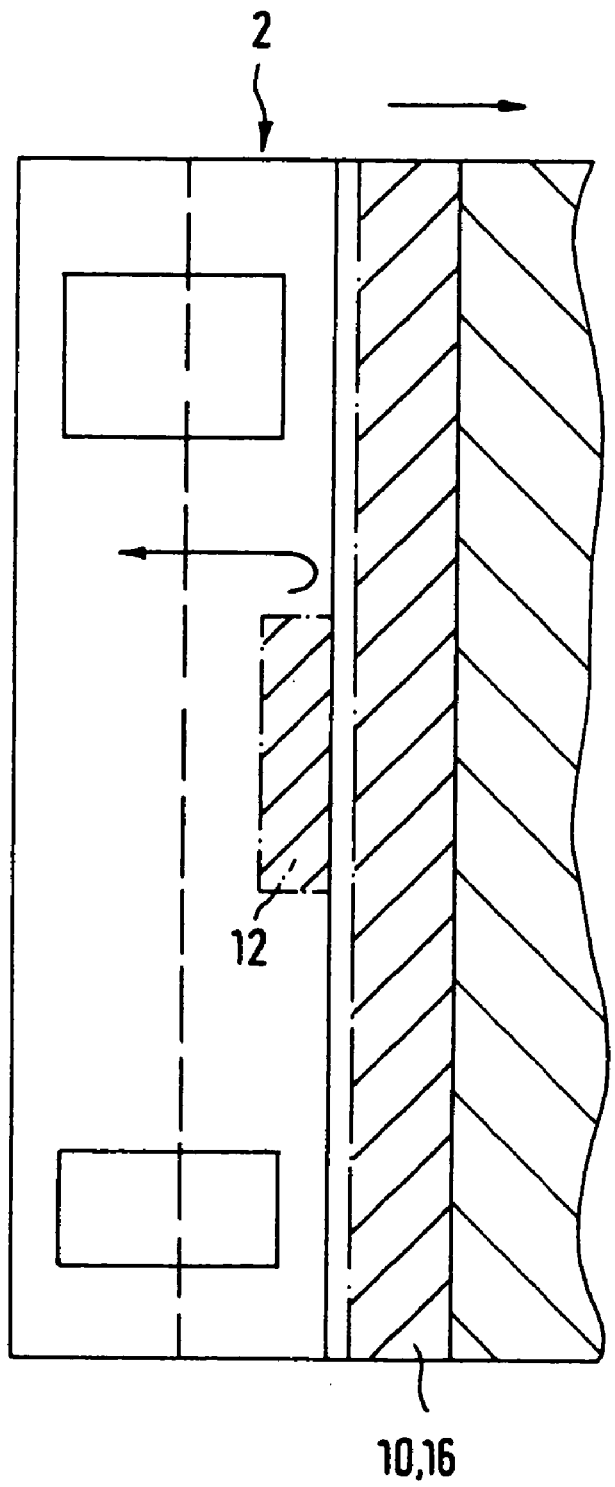
FIG. 1b shows a not-to-scale representation of a section of material in the folded configuration.

Test Preparation:

A material section attached to the main body portion and folded over itself is detached from a hygienic article along a lateral lengthwise edge of the main body portion by breaking the bond. A blade or scissors can be used to do this. The material section 2 forming the lateral part in question is firmly clamped along one lengthwise side edge 4 in accordance with FIGS. 1a and 1b to a lower clamp 6 on the tension testing equipment along the entire lengthwise direction of the incontinence article by which it was previously attached to the main body portion. The lower clamp 6 of the tension testing equipment 8 must therefore be of the appropriate length, expediently 300 mm. The movable clamp 14 of the tension testing equipment 8 is attached on the opposite free lengthwise edge 10 of the separated material section 2, which forms a gripping area 12 at this point, over a length of 60 mm. In the case of a length of material section of less than 160 mm, the material section 2 is attached at the free lengthwise edge 10 over a length of 30 mm to the movable clamp 14. FIG. 1b, which is not to scale, shows the material section 2 in its folded configuration, with the area 16 on the lengthwise edge 10 fixed in the clamp 6 and the gripping area 12 fixed in the clamp 14 shown cross-hatched. The arrows indicate the direction in which the tension testing equipment is pulling. The clamped length $L_{sp}$ is also indicated in FIG. 1a.

A tension test is carried out by means of controlled motion of the movable clamp 14.

Test Parameters:

Test speed of the movable clamp: 300 mm/min

Clamped length: 10 mm

Measurement distance: length of the lateral extension of the unfolded material section Preforce: 0.01 N.

Analysis:

The result of the tension test is given in N rounded to two decimal places as the tensile force occurring in the material section and determined between the clamps. A force/distance graph is generated.

Figure 2:
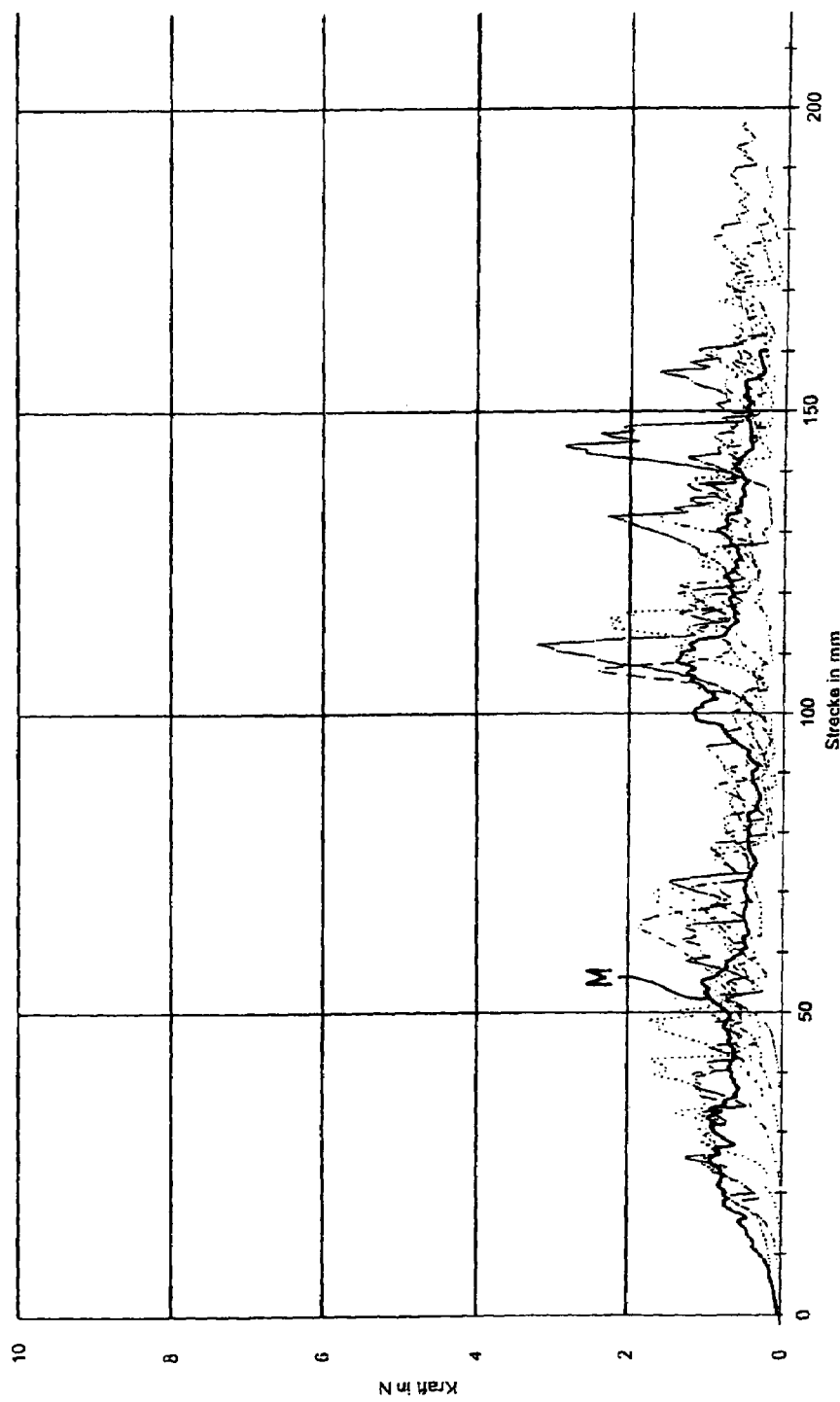
FIGS. 2 and 3 shows force/distance graphs recorded during a tension test.

FIG. 2 shows a force/distance graph of this kind. FIG. 2 shows the results of six tension tests, and the heavy line is an averaged curve M for an incontinence article to be described in what follows. The table below shows the peak forces Fmax and the averages of Fmax determined for a particular unfolding procedure and the average (X(n=6) from the six tension tests. A peak Fmax was assumed if it differed by 0.5 N from an adjacent minimum force.

The table additionally shows the effort in Nmm required for the opening, which was calculated from the tensile forces determined and the distance.

| No. | Average (value) $F_{max}$ in N | $F_{max}$ in N | W in Nmm |
|---|---|---|---|
| 1 | 1.78 | 3.24 | 95.69 |
| 2 | 1.41 | 2.41 | 91.63 |
| 3 | 1.61 | 2.25 | 89.91 |
| 4 | 1.16 | 1.39 | 62.66 |
| 5 | 1.12 | 1.62 | 60.84 |
| 6 | 1.69 | 2.86 | 95.40 |
| x (n = 6) | 1.46 | 2.29 | 82.69 |

The results from FIG. 2 and the table above were determined during the unfolding of material sections which were provided in a back region of a hygienic article in accordance with the invention, which will be described in what follows, where these material sections also have stiffening closures.

Similar measurements were taken on material sections provided in a front region of the hygienic article having a smaller lengthwise extension and without stiffening closures. The results are shown in the same manner in FIG. 3 and in the table below.

| No. | Average (value) $F_{max}$ in N | $F_{max}$ in N | W in Nmm |
|---|---|---|---|
| 1 | 1.05 | 1.48 | 64.67 |
| 2 | 1.20 | 1.77 | 73.73 |
| 3 | 1.52 | 2.54 | 105.45 |
| 4 | 1.73 | 2.49 | 93.93 |
| 5 | 1.32 | 1.88 | 59.04 |
| 6 | 1.10 | 1.30 | 66.19 |
| x (n = 6) | 1.32 | 1.91 | 77.17 |

The incontinence article in accordance with the invention is shown schematically in FIGS. 4 to 7. It comprises a main body portion identified in general by the reference numeral 20, often described as the chassis. The main body portion 20 comprises a front region 22, a back region 24 and a crotch region 26 between them which is positioned between the legs of a wearer when the hygienic article is applied to a wearer. The main body portion 20 comprises an absorbent core 28 which is dimensioned to receive and permanently store bodily fluids in a suitable fashion. The absorbent core 28 has a fluid-impermeable underlayer 30 which can also form the outer visible side of the incontinence article. A fluid-permeable topsheet 32 can be provided above the absorbent core 28, shown in the sectional view of FIG. 5.

In the back region 24 on both sides of the main body portion 20, a material section 34 forming side flaps or lateral sections is attached to a lengthwise edge section 36 of the main body portion 20. To form the lateral sections on both sides, it would also be conceivable that a continuous material section is provided in the transverse direction 38 which forms the two lateral sections of the incontinence article.

Figure 4:
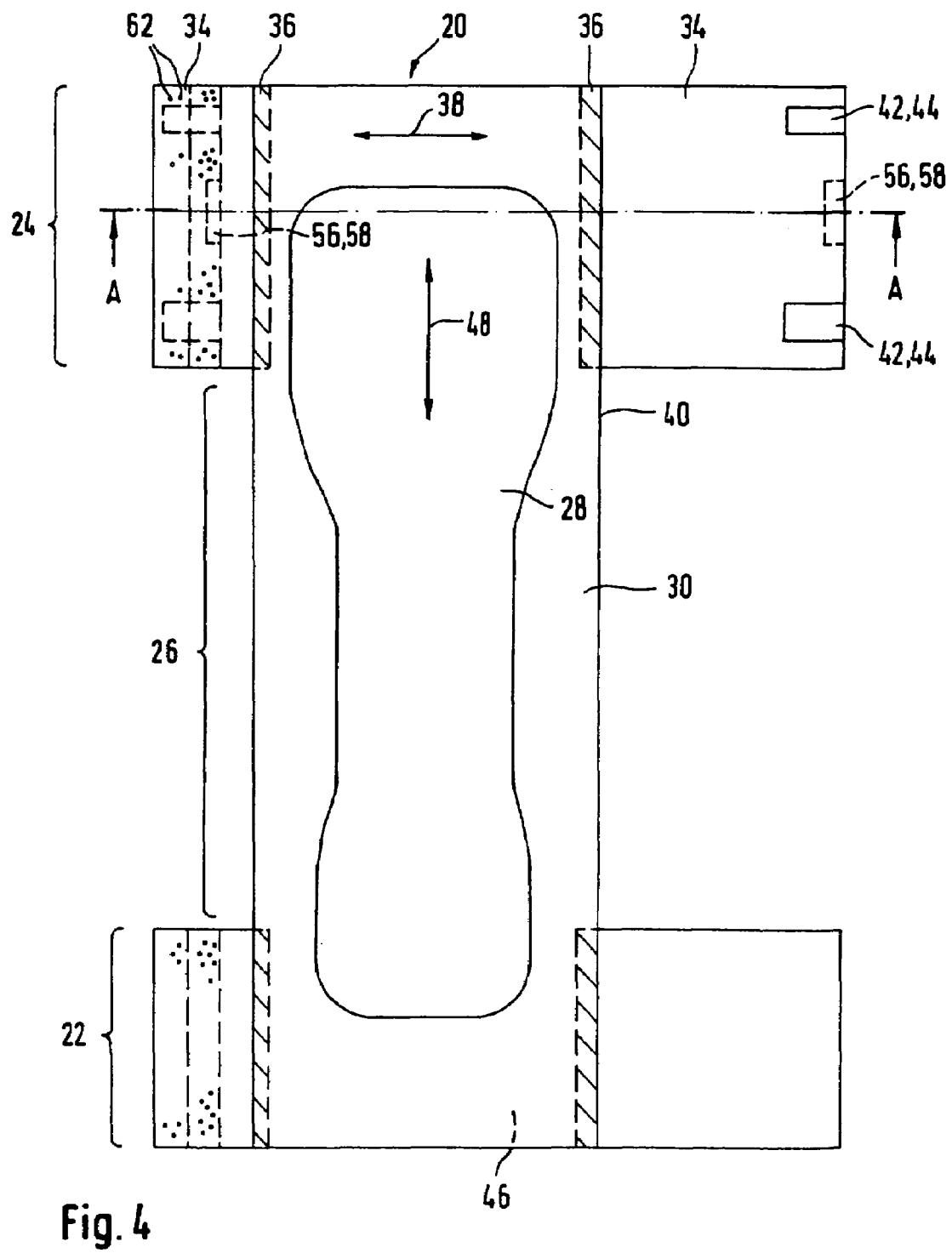
FIG. 4 shows a plan view of a hygienic article in accordance with the invention in a schematic representation.

FIG. 4 shows the right material section 34 in the drawing in its completely unfolded state. It extends in the transverse direction 38 beyond the matching lengthwise edge 40 of the main body portion 20 in the direction encircling the hips. The right material section 34 has two closures 42 in the form of closing tapes 44 folded over themselves which are unfolded when the article is to be used in the intended manner. The tapes 44 interact in a releasably adherent manner with an outside 46 of the front region 22 of the main body portion 20.

Figure 5:
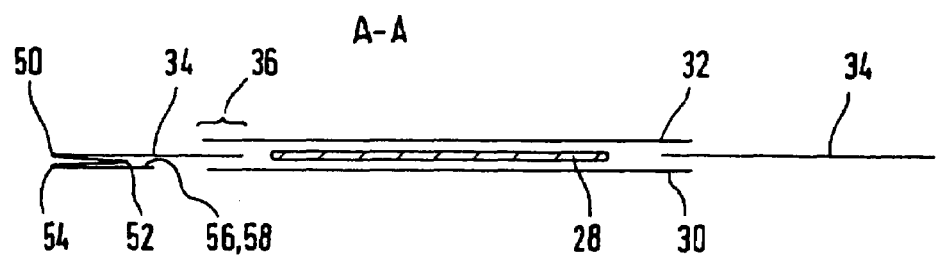
FIG. 5 shows a sectional view of the hygienic article in accordance with FIG. 4 (A-A)
Figure 6:
FIG. 6 shows a sectional view corresponding to FIG. 5 with a folded-in section of material.
Figure 7:
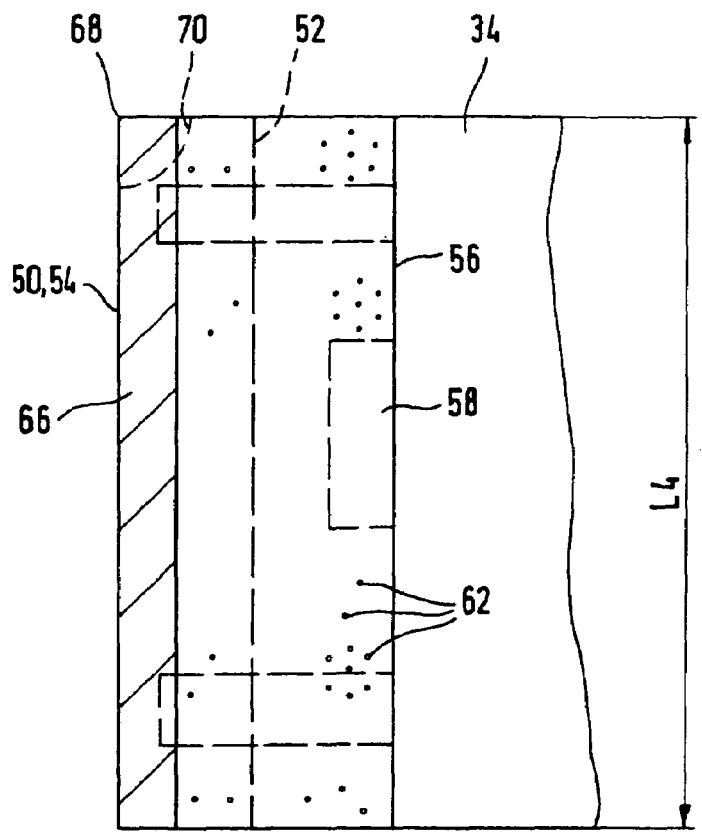
FIG. 7 shows an enlarged representation of a material section in a folded configuration.

Each material section 34 in the back region 24 of the main body portion 20, as can be seen from FIG. 4 in the upper left and the sectional drawing from FIG. 5, is folded over itself in a gate-fold format along three fold lines 50, 52, 54 extending in the lengthwise direction.

A free lengthwise edge section 56 of each material section 34 forms a gripping area 58 for manually grasping the folded material section 34 to unfold said section. When the end user receives the article, the two material sections 34, starting from the representation in FIG. 5, are folded inward into the position indicated in FIG. 6. It can be seen that the free lengthwise edge section 56 and therewith the gripping area 58 of the material section 34 is turned outward from the lengthwise center axis of the incontinence article, so that with the hygienic article spread out on a flat surface a wearer can comfortably grasp the gripping area 58 with the left hand from the left and a correspondingly positioned gripping area 58 on the other material section with the right hand from the right. It could also be contemplated that the material sections 34 folded inward onto the topside of the main body portion partially overlap each other, wherein it proves to be advantageous if, in this overlapping configuration, each of the gripping areas 58 of the material sections 34 can be grasped at the same time.

The folded partial sections 60 of the material sections 34 are releasably attached to each other in the folded configuration by punctiform affixation points 62 generated by ultrasonic welding, with a diameter of 0.35 mm and an area of 0.0962 mm², indicated in FIG. 4. It has been shown that this releasable attachment can be designed in such a way that the material section 34 can be completely unfolded by a single pull on the particular gripping area 58, detaching or separating all the affixation points 62. It proves to be advantageous if no affixation point is provided on the partial sections 60 at a distance of at least 5 mm, preferably of at least 8 mm and even more preferably of at least 10 mm from the fold lines 50, 54. This affixation point-free area is identified in FIG. 7 by reference numeral 66. Starting at point 68 on the fold line 50, 54 farthest from a gripping area 58, no bond point is provided in a schematically indicated area 70. These areas, far removed from the gripping area 58 and located in the proximity of a fold line 50, 54, are particularly critical with respect to complete unfolding, i.e. separation of all affixation points. So it proves advantageous if only a few, or preferably no, affixation points are provided in these critical areas so that the folded material sections can be detached or unfolded with one pull, without reaching back again or having to make repeated abrupt pulls on the gripping area 58.

Figure 8:
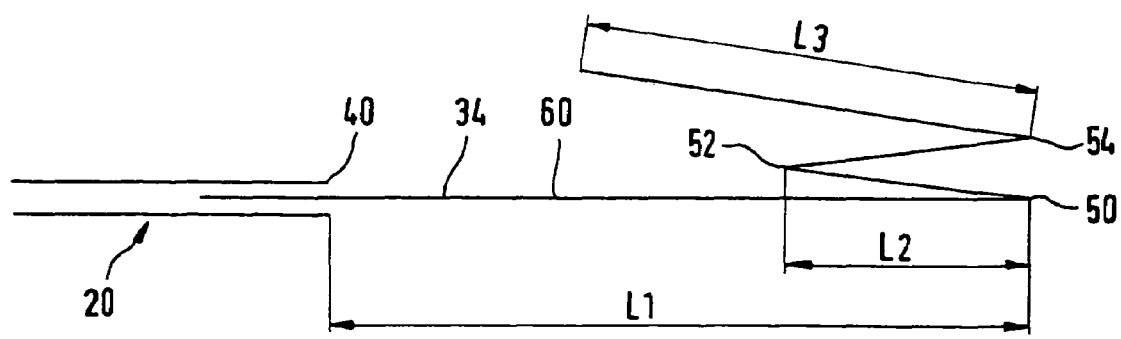
FIG. 8 shows a schematic cross-sectional view of a folded material section.

The dimensions of the partial sections 60 of the material sections 34 are clear from FIG. 8. The extension L1 in the transverse direction 38 from the lengthwise edge 40 of the main part 20 to the fold line measures 90 mm. The extension L2 between the fold lines 50-52-54 measures 35 mm in each case, and the length L3 to the free edge measures 65 mm. The total extension in the transverse direction of the unfolded section of material therefore measures 225 mm in the transverse direction 38. The lengthwise extension L4 measures 260 mm.

As can be seen from FIG. 4, folded material sections 34 with a lengthwise extension L4 of only 200 mm and a transverse extension of 225 mm are similarly provided in the front region 22 of the hygienic article, but do not have any closures which stiffen the sections of material and consequently contribute to the loosening of adjacently located affixation points because of their stiffness. Affixation points or areas can be provided in the immediate proximity of such stiffening closures which are easy to detach because of the stiffening.

Figure 3:
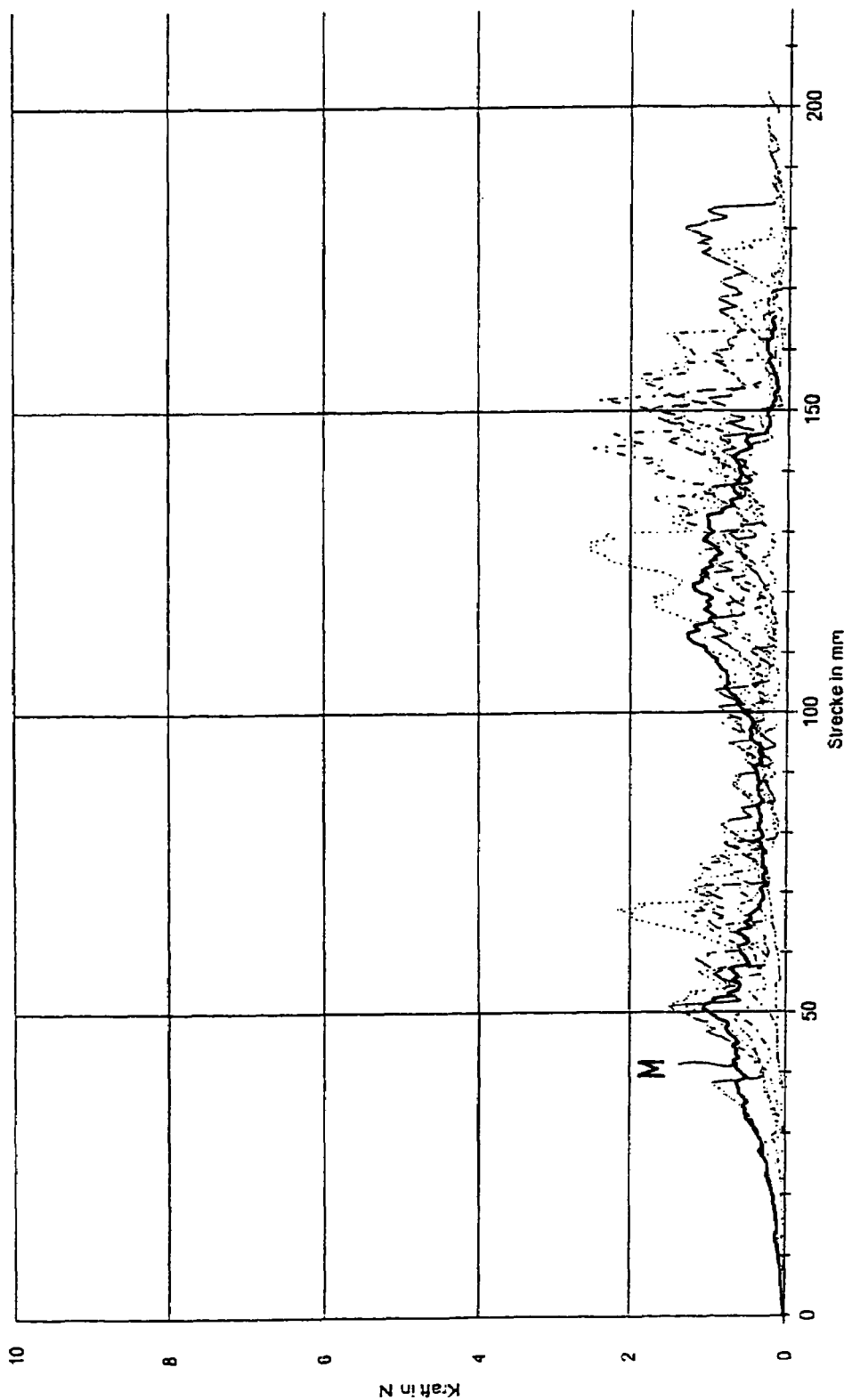

As already mentioned, the measurement results from Table 1 and FIG. 2 were determined during unfolding procedures on the material sections 34 in the back region 24 and the measurement results from Table 2 and FIG. 3 were determined during unfolding procedures on the material sections 34 in the front region 22.

What is claimed is:

1. An absorbent incontinence article having a main body portion, consisting of a front region, a back region and crotch region lying therebetween in a longitudinal direction positioned between the legs of a wearer, wherein the main body portion comprises an absorbent core, and material sections attached to at least one of the back region and to the front region which extend in the transverse direction beyond lateral lengthwise edges of the main body portion and connect the front region and the back region when the article is worn, wherein an extension of the respective material section in the longitudinal direction in the area of attachment to the main body portion measures from between 10 cm and 26 cm, and wherein an extension of the respective material section in the transverse direction beyond the longitudinal edge of the main body portion measures between 10 cm and 35 cm, wherein the respective material sections attached to the back region have closures in the form of closing tapes, wherein the material sections are folded over themselves along at least one fold line running in the lengthwise direction and partial sections of the material sections adjoining one another over an area in the folded configuration are releasably attached to one another at affixation points, wherein a gripping area for unfolding the material section is provided at the center of a lengthwise edge section of the material section, wherein at least one of the number and the relative surface area of the affixation points and the adhesive strength of the releasably attached partial sections of the material sections decreases with distance from the gripping area in the longitudinal direction.

2. The incontinence article of claim 1, wherein the particular partial section has no affixation points in the gripping area.

3. The incontinence article of claim 2, wherein the releasable attachment at all of the affixation points can be separated when unfolding by a single pull on a gripping area of the particular material sections.

4. The incontinence article of claim 1, wherein a folded, material section is folded over itself along at least two fold lines.

5. The incontinence article of claim 4, wherein a folded material section is folded over itself at least along three fold lines.

6. The incontinence article of claim 2, wherein the particular gripping areas are turned outward away from each other in the transverse direction before use in such a way that a wearer can grasp the gripping areas comfortably with the left hand from the left and the right hand from the right.

7. The incontinence article of claim 1, wherein the releasable attachment to each other of the partial sections folded over themselves of the material sections is formed by a plurality of essentially punctiform affixation points.

8. The incontinence article of claim 1, wherein the releasable attachment to each other of the partial sections folded over themselves of the material sections is formed by one of thermally and ultrasonically formed affixation points.

9. The incontinence article of claim 1 , wherein in a compass of 1.5 cm around a point on a most distant fold line farthest removed from the gripping area the adjoining partial sections are not attached to each other.

10. The incontinence article of claim 1, wherein at a distance from 5 mm to 10 mm from the fold line farthest removed from the gripping area, the adjoining partial sections are not attached to each other.

11. The incontinence article of claim 1, wherein a real extension of partial sections folded over each other and adjoining one another can be divided into two approximately equal halves by a straight line running in the longitudinal direction and one of the number and the relative surface area of the affixation points and the adhesive strength of the releasably attached partial sections is different in the two halves.

12. The incontinence article of claim 11, wherein the one of the number and the relative surface area of the affixation points and the adhesive strength of the releasably attached partial sections in the half facing the gripping area in the transverse direction is greater than in the half facing away from the gripping area in the transverse direction.

13. The incontinence article of claim 1, wherein an extension of a material section in the longitudinal direction in the area of attachment to the main body portion measures from at least 10 cm to at least 18 cm and more specifically at least 22 cm.

14. The incontinence article of claim 1, wherein an extension of a material section in the unfolded state in the transverse direction beyond the longitudinal edge of the main body portion measures at least 10 cm to at least 22 cm.

15. The incontinence article of claim 1, wherein the material sections provided on both sides in at least one of the front region and the back region of an article folded prior to use are tucked in on the body-facing side of the main body portion.

16. The incontinence article of claim 15, wherein the material sections partially overlap each other but the respective gripping areas can still be grasped simultaneously.

17. The incontinence article of claim 1, wherein the material sections attached to the main body portion are made from a nonwoven material.

18. The incontinence article of claim 1, wherein the material sections attached to the main body portion are less stiff than the main body portion.

19. The incontinence article of claim 1, wherein affixation points or affixation areas offer a peak resistance averaged over the unfolding process of at most 2.5N maximum, to specifically at most 2.0N when the material sections are unfolded by pulling on the respective gripping area.

20. The incontinence article of claim 1, wherein affixation points offer a peak resistance averaged over six unfolding of from 2.0 N maximum to 1.5 N maximum when the material sections are unfolded by pulling on the respective gripping area.

21. The incontinence article of claim 1, wherein the effort required when unfolding a material section in one pull averaged over six unfoldings measures at most 120 Nmm, specifically at most 90 Nmm.

22. An absorbent incontinence article having a main body portion, consisting of a front region, a back region and a crotch region lying therebetween in a longitudinal direction positioned between the legs of a wearer, wherein the main body portion comprises an absorbent core, and material sections attached to at least one of the back region and to the front region which extend in the transverse direction beyond lateral lengthwise edges of the main body portion and connect the front region and the back region when the article is worn, wherein an extension of the respective material section in the longitudinal direction in the area of attachment to the main body portion measures from between 10 cm and 26 cm, and wherein an extension of the respective material section in the transverse direction beyond the longitudinal edge of the main body portion measures between 10 cm and 35 cm, wherein the material sections attached to the back region have closures in the form of closing tapes, wherein the material sections are folded over themselves along at east one fold line running in lengthwise direction and partial sections of the material sections adjoining one another over an area in the folded configuration are releasably attached to one another at affixation points, wherein a gripping area for unfolding a material section is provided at the center of a lengthwise edge section of the material section, wherein a region of the material sections in the folded configuration in which one of the number and the relative surface area of the affixation points and the adhesive strength of the releasably attached partial sections of the material sections decreases with distance from the gripping area in the transverse direction.

23. An absorbent incontinence article having a main body portion, consisting of a front region, a back region and a crotch region lying therebetween in a longitudinal direction positioned between a legs of a wearer, where the main body portion comprises an absorbent core, and material sections attached to at least one of the back region and the front region which extend in the transverse direction beyond lateral lengthwise edges of the main body portion and connect the front region and the back region when the article is worn, wherein an extension of a material section in the longitudinal direction in the area of attachment to the main body portion measures from between 10 cm and 26 cm, and wherein an extension of a material section in the transverse direction beyond the longitudinal edge of the main body portion measures between 10 cm and 35 cm, wherein the material sections attached to the back region have closures in the form of closing tapes, wherein the material sections are folded over themselves along at least one fold line running in the lengthwise direction and partial sections of the material sections adjoining one another over an area in the folded configuration are releasably attached to one another at affixation points, wherein a gripping area for unfolding a material section is provided at the center of a lengthwise edge section of the material section, wherein an a area extension of partial sections folded over each other and adjoining one another can be divided into two approximately equal halves by a straight line running in the longitudinal direction and wherein one of the number and the relative surface area of the affixation points and the adhesive strength of the releasably attached partial sections in the half facing the gripping area is greater than in the half facing away from the gripping area.

24. The incontinence article of claim 23, characterized by a region of the material sections in the folded configuration in which one of the number and the relative surface area of the affixation points and the adhesive strength of the releasably attached partial sections of the material sections decreases with distance from the gripping area in the longitudinal direction.

* * * * *